United States Patent [19]

Radhakrishnan et al.

[11] Patent Number: 4,895,719

[45] Date of Patent: Jan. 23, 1990

[54] METHOD AND APPARATUS FOR ADMINISTERING DEHYDRATED LIPOSOMES BY INHALATION

[75] Inventors: Ramachandran Radhakrishnan; Paul J. Mihalko, both of Fremont; Robert M. Abra, San Francisco, all of Calif.

[73] Assignee: Liposome Technology, Inc., Menlo Park, Calif.

[21] Appl. No.: 22,937

[22] Filed: Mar. 6, 1987

Related U.S. Application Data

[63] Continuation-in-part of Ser. No. 737,221, May 22, 1985, abandoned, and Ser. No. 860,528, May 7, 1986, abandoned, and Ser. No. 937,609, Dec. 3, 1986.

[51] Int. Cl.⁴ .................... A61K 31/35; A61K 9/14; A61K 9/48; A61K 9/68
[52] U.S. Cl. ........................... 424/45; 514/958; 514/959; 604/140
[58] Field of Search ............... 424/45, 46; 514/956, 514/958, 964, 965

[56] References Cited

U.S. PATENT DOCUMENTS

| | | | |
|---|---|---|---|
| 3,551,558 | 12/1970 | Takebe et al. | 424/46 |
| 3,755,557 | 8/1973 | Jacobs | 424/46 |
| 4,083,953 | 4/1978 | Doria et al. | 424/46 |
| 4,232,002 | 11/1980 | Nogrady | 424/46 X |
| 4,462,983 | 7/1984 | Azria et al. | 424/45 |
| 4,752,466 | 6/1988 | Saferstein et al. | 424/45 X |

FOREIGN PATENT DOCUMENTS

| | | | |
|---|---|---|---|
| 0158441 | 10/1986 | European Pat. Off. | 424/45 |
| 4214804 | 8/1965 | Japan | 424/46 |
| WO86/01714 | 3/1986 | PCT Int'l Appl. | 424/45 |
| 2145107 | 3/1985 | United Kingdom | 424/45 |
| 2166651 | 5/1986 | United Kingdom | 424/46 |

*Primary Examiner*—Floyd D. Higel
*Attorney, Agent, or Firm*—Peter J. Dehlinger

[57] ABSTRACT

A system and method for administering a drug, at a selected dose, via the respiratory tract. Spray-dried liposome particles containing the selected dose of the entrapped drug are released into the air in aerosolized form, either by entrainment in an air or propellant stream, or by release from a pressurized can containing a suspension of the liposomes in a fluorchlorocarbon solvent.

18 Claims, 1 Drawing Sheet

METHOD AND APPARATUS FOR ADMINISTERING DEHYDRATED LIPOSOMES BY INHALATION

This application is a continuation-in-part of U.S. patent applications for "Liposome Inhalation Method and System", Ser. No. 737,221, filed May 22, 1985, now abandoned "Liposome Concentrate and Method", Ser. No. 860,528, filed May 7, 1986, now abandoned and "Liposome Inhalation Method and System", Ser. No. 937,609, filed Dec. 3, 1986 currently pending.

FIELD OF THE INVENTION

The present invention relates to drug delivery by inhalation, and, in particular, to an improved system and method for delivering liposomes containing a metered drug dose via inhalation.

REFERENCES

The following references are incorporated herein by corresponding number:
1. Hollenbeck, R. G., et al, in "Pharmaceutics and Pharmacy Practice" (Banker, G. S., et al, eds), J. P. Lippincott, Philadelphia (1982), pp. 344–358.
2. Szoka, F., Jr., et al, *Ann Rev Biophys Bioeng* (1980), 9: 467.
3. Szoka, F., Jr., et al, *Proc Natl Acad Sci* (USA) (1978) 75: 4194.
4. Hollenbeck, R. G., op cit. pp. 382–391.

BACKGROUND AND SUMMARY

Inhalation provides an effective means for delivering a variety of drugs, including nasal decongestants, drugs useful in the treatment of asthma and other bronchial and pulmonary conditions (1). One advantage of inhalation in treating nasal, bronchial, and pulmonary conditions is the ability to deliver the drug directly to the site of drug action. A related advantage is the rapid onset of the therapeutic effect, compared with other routes of administration, such as intramuscular and oral routes. For drugs which are susceptible to breakdown in the gastrointestinal tract, or which otherwise cannot be administered orally, inhalation may be preferred for a variety of reasons over intravenous or intramuscular injection. Other drugs, such as nitroglycerin, whose primary drug action is systemic, can also be delivered efficiently by inhalation.

Several methods for delivering drugs via inhalation are known. In one, the drug is dissolved in a suitable solvent which can be aerosolized to form a small-particle mist. The drug solution may be aerosolized by pneumatic or ultrasonic nebulizer, or, more conveniently, by means of a self-contained nebulizer containing a pressurized, fluorocarbon propellant. Inhalation of the aerosol mist, i.e., drawing the mist from the mouth or nose into the respiratory tract, acts to deposit the drug-containing aerosol particles on various sites of the respiratory tract, including the upper nasopharyngeal region, the tracheobronchial region, and the pulmonary region. In the latter region, the drug has the opportunity for rapid absorption into the bloodstream for systemic action.

Also well known in the prior art are inhalation systems in which a drug is administered in particulate form, either as a dry powder or as a micronized suspension in a suitable carrier solvent system. Typically the drug is a water-soluble compound which is suspended in micronized form in a fluorocarbon-type propellant solvent. Following aerosolization, most of the propellant solvent is lost through flash evaporation and replaced by moisture in the respiratory tract, leading to the deposition of hydrated micronized particles.

Both types of inhalation systems mentioned above are based on delivery of the drug in a free form to sites in the respiratory tract. As such, the drug is rapidly utilized and, in the case of pulmonary deposition, taken up systemically at the site of deposition. Because of this rapid drug uptake and utilization, the drug effect may be relatively short-lived, requiring frequent dosing. A related problem is the limited amount of drug that can be administered safely at each dosing, particularly where the drug has unwanted systemic side effects. This problem is illustrated by a number of $\beta_2$-adrenergic agonist type brochodilators which also produce marked tachycardia. Even at relatively low doses of these drugs, the stimulatory effect of the drug on the heart and other side effects, such as dizziness and insomnia, are a nuisance to the patient. Additionally, micronized particles may irritate the respiratory tract.

More recently, liposome inhalation systems for administering a drug to the respiratory tract in liposome-entrapped form have been proposed. UK patent application GB 2,145,107A describes an aerosol device which brings aqueous and organic-solvent phase solutions together under pressure, and passes the mixture through a nozzle to form aerosolized liposomes. EPO patent application 0,158,441 discloses liposome formation, in aerosol form, from a water/lipid/ethanol mixture. In PCT application WO 86/01714, it is proposed to spray lipid droplets in a volatile liquid carrier, with liposome formation occurring upon contact of the droplets with a moist aqueous surface. UK patent application GB 2,170,815 describes a system in which an aqueous solution is emulsified in a lipid-containing propellant solvent, then sprayed through an atomizing nozzle to form lipid-coated droplets which can form liposomes upon contact with a moist surface. All of these approaches are characterized by "in situ" liposome formation, i.e., liposome formation at the spray valve or on contact with the moist surface of the lungs. As such, the concentration and size of the liposomes formed, and the percentage of drug entrapment in the liposomes, will vary from one dose delivery to another, depending upon temperature and humidity conditions, the extent of solvent mixing, and the total and relative amounts of solvent components present in the system. Thus each of these systems would be difficult to adapt for metered dose delivery, in which a reproducible amount of liposome-encapsulated drug is needed.

SUMMARY OF THE INVENTION

Co-pending patent application for "Liposome Inhalation Method and System" Ser. No. 737,221, filed May 22, 1985, now abandoned, discloses a lipsome-based aerosol system for delivering a drug, at a controlled release rate, via the respiratory tract. The invention is based on two discoveries: First, that rapid systemic uptake of drugs from the site of administration in the respiratory tract can be eliminated or greatly reduced by administering the drug in a predominantly liposome-encapsulated form. Secondly, it was found that the rate of release of a water-soluble drug from a drug/liposome composition delivered to the respiratory tract can be modulated according to the acyl-chain composition of the phospholipids making up the liposomes. As a rule, slower drug release rates correlate with longer in vitro drug efflux half lives in serum. The liposome aerosol compositions used in these studies were prepared under conditions in which the drug was predominantly in liposome-encapsulated form, and the liposome suspensions were delivered in metered dose form from a fixed-volume nebulizer.

Co-owned patent application for "Liposome Concentrate and Method", Ser. No. 860,528, filed Apr. 22, 1986, now abandoned addresses another aspect of effective drug delivery in a liposome-based inhalation system: that of delivering a water-soluble, liposome-permeable drug in predominantly encapsulated form, from a dilute aqueous liposome suspension. The method of the invention involves preparing and storing a liposome/drug suspension initially in paste form, then diluting the paste to a concentration suitable for aerosolizing.

Co-owned U.S. patent application Ser. No. 937,607, filed Dec. 3, 1986, currently pending additionally showed that administration of the $\beta_2$-agonist metaproteranol sulfate (MPS) in liposomal form via inhalation reduced initial plasma levels of the drug more than about 8 fold with respect to free drug, and that plasma levels remained substantially constant over a two hour period, compared with a rapid drop in plasma levels of the drug administered by inhalation in free form. At the levels of MPS which were studied, the percent protection against bronchoconstriction provided by the drug was about the same for both free drug and liposomal-entrapped drug.

It was further discovered, according to the teaching of co-owned patent application for "Liposome Bronchodilator System and Method", Ser. No. 022,669, filed Mar. 6, 1987, that $\beta_2$-adrenoreceptor agonists, when administered in liposome-entrapped form at a therapeutic drug dose (i.e., minimum dose required for optimal or near-optimal short-term therapeutic effect), produce significantly greater bronchodilation, over an extended time period, than is produced by the the same amount of $\beta_2$-agonist delivered to the respiratory tract in a free-drug aerosol form.

The inventions mentioned above show that liposome drug delivery by inhalation provides advantages of (a) reduced side effects due to rapid systemic drug uptake, (b) improved therapeutic action over an extended period, and (c) the ability to modulate rate of drug release from the target site.

The present invention is concerned with a self-contained apparatus, or system and method for delivering a selected amount of drug, efficiently and reproducibly, in liposome encapsulated form. The apparatus of the invention includes liposome particles which have been formed by spray drying a dilute aqueous suspension of the liposomes. The particles formed (a) have a fine particle size, (b) retain the majority of their originally encapsulated material, and (c) are stable, in a preferred formulation, when suspended in a fluorochlorocarbon solvent. The particles are preferably formed, according to one method of the invention, by forming the liposomes from partially or totally saturated phospholipid components and drying the liposomes in a stream of heated gas whose temperature does not degrade the lipid components or structural integrity of the liposomes.

The apparatus further includes a self-contained delivery device for producing an airborne suspension of the liposome particles containing a metered dose of drug, in liposome-entrapped form. In one embodiment, the liposomes are contained in a suspension of a pressurized fluorochlorocarbon solvent in a metered-dose spray device designed to release a selected volume of the suspension in aerosolized form.

In a second embodiment, the liposomes and a metered amount of the liposome-entrapped drug are contained in individual packets. The delivery device may be a propellant spray device designed to release a stream of aerosolized propellant particles through the packet, to entrain the liposomes in the stream. Alternatively, the delivery device may be a flow-through air chamber designed to support a liposome packet such that the liposomes are entrained in a stream of air drawn through the chamber.

These and other objects and features of the present invention will be more fully understood when the following detailed description of the invention is read in conjunction with the accompanying drawings.

DETAILED DESCRIPTION OF THE INVENTION

I. Spray-Dried Liposome Particles

Figure 1A:
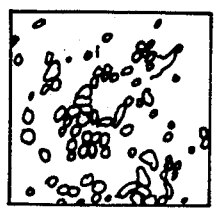
FIGS. 1A and 1B are renderings of light micrographs of spray dried liposomes which have been suspended in a propellant solvent and sprayed onto a dry (1A) or moist (1B) slide.
Figure 1B:
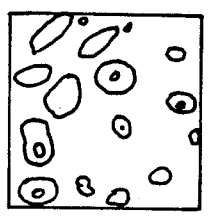

This section discusses methods for preparing spray dried liposomes having desired properties in the inhalation system of the invention. The most important of these properties are (a) high drug entrapment, (b) selected pharmacokinetic behavior when delivered to the respiratory tract, (c) ability to form fine particle sizes on spray drying, and (d) stability on storage in dehydrated or propellant suspension form. Section IA below discusses lipid composition factors which are important to drug release rates, most compatible with spray drying, and give greatest storage stability. Sections IB describes several methods for forming lipsomes containing entrapped water-soluble or lipid-soluble drugs. Spray drying methods are discussed in Section IC.

A. Liposome Components

The effect of liposome lipid components on the rate of drug release in the respiratory tract has been reported in the above-cited co-pending patent applications. Briefly, studies on in vitro drug release rates, as a function of lipid composition in the liposomes, showed that liposomes whose phospholipid components contain longer and/or more saturated acyl chain moieties have longer drug-release half lives. The drug-release rates ranged from less than about 0.5 hour for soy phosphatidylcholine (SPC) to nearly ten days for a mixture of distearoyl PC/distearoyl phosphatidyl glycerol (DSPC/DSPG). The most significant increases in drug release rates were observed when the liposomes contained a significant proportion of lipids whose transition temperature ($T_c$) are above the temperature at which the efflux half lives are measured, e.g., 37+ C.

Studies on the effect of lipid charge on drug release rates indicated that the addition of a negatively charged lipid, such as phosphatidyl glycerol (PG), at a mole ratio of about 10%, produces a slight to moderate increase in efflux half life. The lipid-charge effect is dependent somewhat on the degree of saturation and chain length in the charged and uncharged lipids used in forming the liposomes, with the charge effect producing a greater increase in drug efflux half life where the liposomes are formed of predominantly shorter and/or unsaturated lipids, and producing less effect in the case of longer-chain and/or saturated lipids. The effect of sterol components, such as cholesterol, was relatively minor, and generally followed the known fluidizing effect of sterol on liposomal membranes. That is, in relatively fluid membranes, where sterol increase membrane rigidity, drug-release half lives were increased, and in more rigid membranes, where sterol have a fluidizing effect, drug release half lives were decreased.

Another important consideration in the choice of lipid components is the phase transition temperature of the lipids, which may be greater than the temperature of heated gases used in drying the liposomes such that the drug is retained in liposomes on drying. Most efficient drying temperatures are at least about 37° C., and preferably between about 40°-50° C., although higher temperatures are also possible. Table 1 below gives the transition temperatures and acyl chain composition for a number of different liposome lipid components.

As can be appreciated from the table, liposomes can be formulated with mixtures of relatively low and relatively high phase transition temperature components, to achieve an overall phase transition temperature in the 37° to 50° C. range. Alternatively, partially hydrogenated lipid components, such as PHPC, are suitable when used in combination with other components. The transition temperature of liposomes formed with the selected lipid components can be determined conventionally by differential scanning calorimetry (2).

TABLE 1

Some Properties of Phospholipids Used in Liposomes

| Lipid | Abbrev. | Charge | Tc (°C.) | Ref. |
|---|---|---|---|---|
| Egg phosphatidylcholine | EPC | 0 | −15 to −7 | 109 |
| Dilaurylolylphosphatidylcholine (C12:0) | DLPC | 0 | −1.8 | 122 |
| Dimyristoylphosphatidylcholine (C14:0) | DMPC | 0 | 23 | 109 |
| Dipalmitoylphosphatidylcholine (C16:0) | DPPC | 0 | 41 | 109 |
| Distearoylphosphatidylcholine (C18:0) | DSPC | 0 | 55 | 109.1 |
| 1-Myristoyl-2-palmitoylphosphatidyl-choline (C14:0.16:0) | MPPC | 0 | 27 | 97 |
| 1-Palmitoyl-2-myristoyl phosphatidyl-choline (C16:0.14:0) | PMPC | 0 | 35 | 97 |
| 1-Palmitoyl-2-stearoyl phosphatidyl-choline (C16:0.18:0) | PSPC | 0 | 44 | 97 |
| 1-Stearoyl-2-palmitoyl phosphatidyl-choline (C18:0.16:0) | SPPC | 0 | 47 | 97 |
| Dioleoylphosphatidylcholine (C18:1) | DOPC | 0 | −22 | 109 |
| Dilaurylolylphosphatidylglycerol | DLPG | −1 | 4 | 46 |
| Dimyristoylphosphatidylglycerol | DMPG | −1 | 23 | 158 |
| Dipalmitoylphosphatidylglycerol | DPPG | −1 | 41 | 86 |
| Distearoylphosphatidylglycerol | DSPG | −1 | 55 | 153 |
| Dioleoylphosphatidylglycerol | DSPG | −1 | −18 | 46 |
| Dimyristoyl phosphatidic acid | DMPA | −1 | 51 | 86 |
| Dimyristoyl phosphatidic acid | DMPA | −2 | 45 | 153 |
| Dipalmitoyl phosphatidic acid | DPPA | −1 | 67 | 153 |
| Dipalmitoyl phosphatidic acid | DPPA | −2 | 58 | 153 |
| Dimyristoyl phosphatidylethanolamine | DMPE | — | 50 | 153 |
| Dipalmitoyl phosphatidylethanolamine | DPPE | — | 60 | 203 |
| Dimyristoyl phosphatidylserine | DMPS | — | 38 | 203 |
| Dipalmitoyl phosphatidylserine | DPPS | — | 51 | 120 |
| Brain phosphatidylserine | PS | — | 6–8° | 86 |
| Brain sphingomyelin | BSP | 0 | 32 | 191 |
| Dipalmitoyl sphingomyelin | DPSP | 0 | 41 | 18 |
| Distearoyl sphingomyelin | DSSP | 0 | 57 | 42 |

Other lipid components, including PG, and cholesterol, can be included. In general, cholesterol has a fluidizing effect in liposomes containing predominantly saturated phospholipid components, and thus is expected to lower phase transition temperature slightly. The effect of added PG or other phospholipid components will, of course, depend largely on the acyl chain composition of the lipids.

The liposomes may also be formulated to include various types of drug-protective or lipid-protective agents, such as the antioxidant α-tocopherol, which is typically included at a mole ratio of between about 0.1–2 mole percent.

B. Liposome Preparation

The liposomes are prepared initially as a dilute aqueous suspension which is suitable for spray drying. The suspension may be prepared by a variety of techniques, such as those detailed in reference 2. The choice of the liposome preparation method will depend, in part, on the nature of the drug to be entrapped. As defined herein, "drug" is intended to include any pharmacologically active agent which has a site of action in the respiratory tract or is therapeutically active when it is taken up systemically from the respiratory tract. Such drugs may include antibiotics, peptide hormones, enzymes, enzyme inhibitors, anti-tumor agents, bronchodilators, allergens, antihistamines, and biogenic compounds such as steroids and prostaglandins.

For purposes of discussion, two general classes of drugs will be considered. The first class are predominantly water-soluble drugs which tend to partition into the aqueous phase of a water/oil two-phase system. More particularly, this class of drugs tend to partition preferentially in the aqueous interior phase of liposomes, rather than in the lipophilic bilayer phase. Drugs in this class include relatively small, liposome-permeable drugs such as albuterol (salbutamol) sulfate, ephidrine sulfate, ephidrine bitartrate, isoetharine hydrochloride, isoetharine mesylate, isoproteranol hydrochloride, isoproteranol sulfate, metaproteranol sulfate, terbutaline sulfate, procaterol, and bitolterol mesylate, atropine methyl nitrate, cromolyn sodium, propranalol, fluoroisolide, ibuprofin, gentamycin, tobermycin, pentamidine, penicillin, theophylline, bleomycin, etoposide, captopril, n-acetyl cysteine, and verapamil; and relatively large, liposome-impermeable drugs, such as peptide hormones, enzymes, enzyme inhibitors, apolipoproteins, and higher molecular weight carbohydrates, as exemplified by calcitonin, atriopeptin, $\alpha$-1 antirypsin (protease inhibitor), interferon, oxytocin, vasopressin, insulin, interleukin-2, superoxide dismutase, tissue plasminogen activator (TPA), plasma factor 8, epidermal growth factor, tumor necrosis factor, lung surfactant protein, and lipocortin.

The second general class of drugs are lipophilic drugs which partition preferentially in the oil phase of a water/oil system, and more particularly, preferentially in the bilayer region of liposomes. Representative drugs in this class include prostaglandins, amphotericin B, progesterone, isosorbide dinitrate, testosterone, nitroglycerin, estradiol, doxorubicin, beclomethasone and esters, vitamin E, cortisone, dexamethasone and esters, DPPC/DPPG or any other lipid/surfactant (to relieve RDS), and betamethasone valerete.

One preferred method for preparing drug-containing liposomes is the reverse phase evaporation method described in reference 3 and in U.S. Pat. No. 4,235,871. In this method, a solution of liposome-forming lipids is mixed with a smaller volume of an aqueous medium, and the mixture is dispersed to form a water-in-oil emulsion. The drug to be entrapped is added either to the lipid solution, if a lipophilic drug, or in the aqueous medium, if a water soluble drug. After removing the lipid solvent by evaporation, the resulting gel is converted to liposomes, with an encapsulation efficiency, for a water-soluble drug, of up to 50%. The reverse phase evaporation vesicles (REVs) have typical average sizes between about 1–5 microns and are predominantly oligolamellar, that is, contain one or a few lipid bilayer shells. The oligolamellar nature of the vesicles may facilitate drug efflux and thus contribute to a lower efflux half live for an encapsulated drug.

A simple lipid-hydration procedure for producing multilamellar vesicles (MLVs) may be preferred where high drug encapsulation efficiency is not desired. In this procedure, a mixture of liposome-forming lipids dissolved in a suitable solvent is evaporated in a vessel to form a thin film, which is then covered by an aqueous solution of the drug. The lipid film hydrates to form MLVs, typically with sizes between about 0.1 to 10 microns. As in the REV method, the drug to be encapsulated is added either to the initial lipids or to the hydrating medium, depending on its solubility in water. The percent of total drug material which can be encapsulated in the MLVs, calculated as the ratio of encapsulated drug to total drug used in vesicle preparation, is typically between about 5–20% for water-soluble drugs.

It is mentioned here, for the case of lipid-soluble drugs, and where spray-dried liposomes are suspended in a fluorochlorocarbon solvent which is itself a solvent for the drug, that the drug may be included initially in the propellant solvent rather than in the liposomes. In this embodiment, the spray dried liposomes are formed without added drug, with the drug being incorporated into the lipid vesicles at the time of contact with and evaporation of the solvent in an aerosol. This system will be described in Section II below.

The liposome preparation methods described above produce heterogeneous liposomes sizes, typically ranging from less than about 0.1 micron to up to about 20 microns in size. Optimal liposome size, after spray drying, is preferably less than about 5 microns, although respirable particles as large as 5–8 microns are suitable. The size of the liposomal particle formed on dyring the liposomes in suspension will depend both on the initial size of the aqueous-suspension liposomes and on the degree of liposome aggregation which occurs on drying. As will be seen below, liposomes having an initial suspension size of about 1.5 microns produce particles ranging from about 1.5 to 4 microns on drying. In general, therefore, it is desirable to process liposomes formed by either of the above two methods to reduce the largest liposomes to less than about 2 and preferably 1.5 microns. Liposome sizing can be achieved by extruding an aqueous suspension of the liposomes through a polycarbonate membrane having a selected uniform pore size, typically 1 micron or less (reference 3). A more recent method for sizing liposomes involves extrusion through an asymmetric ceramic filter. The method is detailed in co-owned U.S. patent application for Liposome Extrusion Method, Ser. No. 829,710, filed Feb. 13, 1986, now U.S. Pat. No. 4,737,323.

In the case of an encapsulated water-soluble drug, the liposomes may be further treated to remove non-encapsulated drug from the suspension. Conventional separation techniques, such as centrifugation, diafiltration, and molecular-sieve chromatography are suitable. The separation step should be carried out after sizing, since the sizing procedure itself can lead to liposome rupture and release of encapsulated drug. It will be appreciated that in the case of a water-soluble liposome-permeable drug which can rapidly equilibrate between encapsulated and bulk-phase aqueous spaces in the liposomal suspension, drug removal needs to be carried shortly before spray drying, i.e., before appreciable leakage of the drug from the liposomes.

It is also possible, using recently-developed liposome preparation methods (detailed in co-owned U.S. patent applications for "High-Concentration Liposome Processing System and Method" Ser. No. 909,122, filed Sept. 18, 1986, now U.S. Pat. No. 4,781,781, issued November 1988 and "High-Encapsulation Liposome Processing System and Method" Ser. No. 908,765, filed Sept. 18, 1986), now U.S. Pat. No. 4,752,425, issued June 21, 1988, to prepare a liposome suspension which (a) has maximum sizes of about 1.5 microns or less and (b) contains at least about 50%, and typically 70% or more, of the drug in liposome-entrapped form. Thus, liposomes produced by these methods do not need to be further sized or treated to remove free drug. In this method, a solution of lipids (and lipid-soluble drug, if such is used) is injected in an organic solution into an aqueous buffer (and a water-soluble drug, if such is used) under selected temperature and pressure conditions, with liposome formation in the aqueous medium. Lipid injection into the liposome suspension is continued until a final lipid concentration of at least about 250 mM and preferably between about 300–500 mM is reached. At this lipid concentration, the liposomes are predominantly in the size range below about 1.5 microns, and up to 70% or more of the drug is associated with the liposomes, either in encapsulated form in the case of a water-soluble drug, or in membrane-entrapped form in the case of a lipid-soluble drug. The final suspension may have a paste-like consistency. The paste may be diluted to a selected concentration, as described below, immediately before spray drying.

C. Spray Drying

A liposome suspension prepared as above is diluted, if necessary, to a final dilute suspension which is suitable for spray drying. The suspension has the following preferred characteristics:

a. a liposome concentration of between about 2–10 and preferably 3–6 weight percent;

b. More than half and preferably about 70% or more of the total drug in liposome-entrapped form, either liposome-encapsulated form, in the case of a water-soluble drug, or membrane associated form, in the case of a lipid-soluble drug; and c. maximum liposome sizes less than about 2 and preferably 1.5 microns;

The final salt concentration, and osmolarity, of the suspension may be adjusted to achieve desired liposome stability and avoid high salt concentrations on liposome administration. Where the liposomes contain a high concentration of an encapsulated drug, it is generally desirable to balance the high internal osmolarity of the liposomes with an equivalent osmolarity in the bulk phase of the suspension. Typically, this may be done by forming the suspension in phosphate buffered saline (PBS) (about 300 mOs) and adding salt to raise the osmolarity to the desired level, e.g., 380 mOs. The suspension can be diluted or desalted, immediately before spray drying, to a reduced osmolarity, e.g., 150–300 mOs. Alternatively, particularly in the case drug osmotic effects are not large, the suspension can be diluted or desalted to a low ionic strength. The advantage of the low-ionic strength buffer is that the final salt concentration of the dried liposomes is relatively low, thus minimizing hypertonic salt effects which may occur when the dried liposomes are hydrated in the lungs.

The osmolarity of the suspension may also be adjusted by the presence of a bulking agent, such as lactose or other sugar. The bulking agent, which is typically added between about 2–7 percent by weight, may also facilitate spray drying, both by drawing water from the liposomes in the terminal stages of drying, and by reducing the tendency of liposomes to aggregate during the drying procedure.

The liposome suspension can be spray dried in a conventional drying apparatus in which the material to be dried is sprayed in aerosolized form into a stream of heated air or inert gas, and the aerosolized liposome particles are dried in the gas stream as they are carried toward a plate collector where the dried liposomes are collected. An exemplary spray dry apparatus which is suitable for use in the present invention is a Buchi 190 Mini Spray Dryer.

As noted above, the drying temperature is at least about 37° C., and preferably higher than 40° C. More particularly, the drying temperature is such that the liposomes remain in a rigid, unmelted state during the heating process. The temperature of the collection chamber is generally lower than that of the heated air, and typically about 37° C.

By way of examples, liposomes formed from PHPC:cholesterol:Pc (5:4:1) and containing 1 mole percent $\alpha$-tocopherol were formed by a solvent injection into an aqueous metaproteranol sulfate (MPS) solution (100 mg/ml), to a final liposome concentration of about 400 $\mu$mole/ml and a final encapsulation efficiency of about 70%. The liposomes, which had maximum sizes of about 1.5 microns, were diluted to 3 percent by weight in low osmolarity phosphate buffer, pH 7.4, and spray dried at about 48° C. The size and stability characteristics of the liposomes are discussed in Section II below.

The dried liposomes are collected and stored in dehydrated form, at lower temperature (typically 4° C.).

II. Delivery Devices

This section describes three self-contained delivery devices designed for producing an airborne suspension of the spray dried liposome particles. As defined herein "self-contained" means that the liposome aerosol is produced in a self-contained device that it propelled by a pressure differential created either by release of a pressurized fluorochlorocarbon propellant or by a stream of air drawn through or created in the device by the user. The devices described in parts A and B both employ propellant solvents for aerosolization; the device of part C employs a stream of air drawn through the device by the user.

A. Liposome/Propellant Suspension

This apparatus, or system uses a conventional pressurized propellant spray device for delivering a metered amount of spray dried liposomes which are suspended in the propellant. Since the system requires long-term suspension of liposomes in a suitable propellant, the liposomes and propellant components of the suspension must be selected for liposome stability on storage. To this end, the liposomes are preferably formed of partially or totally hydrogenated lipid components. Consistent with this, the lipids chosen must be such that the dried liposomes remain integral in the propellant solvent at the anticipated storage temperature of the pressurized solvent. This condition is usually met by the constraints imposed by the spray drying process.

Several fluorochlorocarbon propellant solvents have been used or proposed for self-contained inhalation devices. Representative solvents includes "Freon 11" ($CCl_3F$), "Freon 12" ($CCl_2F_2$), "Freon 22" ($CHClF_2$), "Freon 113" ($CCl_2FCClF_2$), "Freon 114" ($CClF_2CClF_2$), and "Freon 115" ($CClF_2CF_3$), as well as other fluorochloro substituted methyl and ethyl compounds. Earlier studies carried out by the inventors have examined the stability of of various liposome formulations when an aqueous suspension of the liposomes is emulsified, for an extended shaking period, in each of the six Freon solvents mentioned above. The liposomes were monitored for change in size and loss of encapsulated bovine serum albumin or carboxyfluroescein after exposure to the selected solvent. Best liposome stability, in terms of both size stability and retention of encapsulated material, was achieved with Freon 114 and 115. These solvents produced little liposome disruption, even with liposomes composed predominantly of unsaturated lipids. Greatest liposomes disruption was seen with Freon 22. Freons 11, 12, and 113, showed intermediate results, with the more saturated liposome formulation showing substantially greater stability in these solvents.

Studies carried out in support of the present invention have examined the stability and size characteristics of spray dried liposomes in several Freon propellents. Here liposomes containing PHPC:cholesterol:PG (5:4:1) with 1 mole percent α-tocopherol (formed as described above) were spray dried from a 3 percent by weight solution, either in the presence or absence of 5 weight percent lactose, under spray drying conditions discussed above. The dried liposome particles were maintained in suspension with a selected propellant solvent at room temperature for a several-day period, then collected by spraying onto a plate. The propellants used were Freons 12, 113, 114, and 115.

Figure 2A:
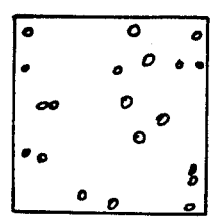
FIGS. 2A and 2B are renderings of light micrographs of liposomes, as in FIGS. 1A and 1B, respectively, but where the liposomes were spray dried from a 5% lactose solution.

FIG. 1A is a rendering of a light micrograph of liposomes suspended in Freon 115, then collected by spraying onto a dry plate. As seen, the liposomes are present in both single and aggregated form. The sizes of the larger aggregates observed is about 10 microns, and the single liposomes are less than about 1 micron in size. The appearance of the same liposome material, when sprayed onto a moist plate is seen in FIG. 2A, which shows the liposomes in a hydrated condition. The liposomes are predominantly unaggregated, and have a size range between about 0.1 and 5 microns. It is thus seen that (a) spray dried liposomes can be maintained in stable form in Freon solvent and (b) rehydrated, on contact with a moist surface, to form bilayer vesicles.

Figure 2B:
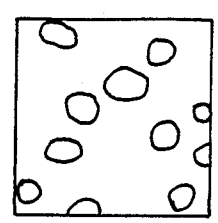

FIGS. 2A and 2B show the appearance of the liposomes having the same lipid composition but prepared and spray dried from a suspension containing 5% lactose. The spray dried liposomes were suspended, as above, in Freon 115, then sprayed onto either a dry (2A) or moist (2B) plate. The condition of the liposomes appears to less aggregated than in the absence of lactose. The dried particles clearly form liposomes on rehydration, with liposome sizes predominantly less than about 5 microns.

Similar results were observed with spray dried liposomes suspended for extended periods in Freon 12, 113, and 115.

The effect of propellant solvents on drug encapsulation in liposomes was also studied. Briefly, liposomes containing encapsulated metaproteranol sulfate (MPS) were prepared by solvent injection, diluted and spray dried. On rehydration, about 50% of the drug was present in encapsulated form, as determined by the concentration of MPS after liposome removal by centrifugation. The spray dried liposomes were also suspended in Freon 115 or Freon 114, and after a several-day storage period, were sprayed onto a moist plate for rehydration. The amount of encapsulated drug on rehydration was again about 50%, indicating that suspension in Freon 115 did not produce appreciable loss of encapsulated drug.

To form the liposome/propellant suspension, the spray-dried liposomes are added to the selected propellant or propellant mixture, to a final liposome concentration of about 1 to 30, and preferably between about 10–25 percent by weight percent by weight of the total propellant. Where the drug is a water-soluble compound which is included and remains encapsulated in the spray-dried liposomes in the propellant suspension, the final concentration of liposomes in the propellant is adjusted to yield a selected metered dose of the drug, in a given aerosol suspension volume. Thus, for example, if the liposomes are formulated to contain 0.05 mg dru per mg dried liposomes, and the selected dose of drug to be administered is 1 mg, the suspension is formulated to contain 20 mg of dried liposomes per aerosol dose.

For a lipid-soluble drug, i.e., one which is readily soluble in the propellant solvent, two formulation approaches are possible. In the first, the drug is initially included in the lipids used in forming the spray dried liposomes, and these are then added to the propellant in an amount which gives a selected concentration of drug/volume of propellant, as above. Alternatively, the drug may be added initially to the solvent, at a selected drug concentration. The liposomes in this formulation are "empty" spray dried liposomes which will act as a lipid reservoir for the drug during aerosol formation and solvent evaporation. The final concentration of empty liposomes is adjusted to give a convenient total lipid dose which is suitable for holding the metered amount of drug.

Figure 3:
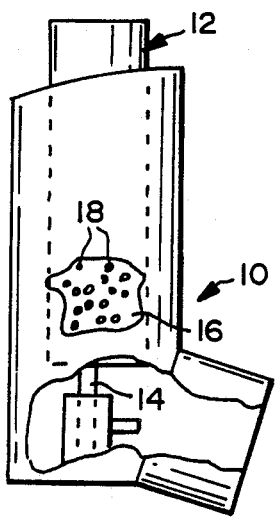
FIG. 3 is a side cutaway view of a liposome delivery apparatus according to one embodiment of the invention, in which spray-dried liposomes are delivered from a suspension in a pressurized propellant.

The suspension is packaged in a conventional self-contained propellant device, such as the one shown at 10 in FIG. 3. The device generally includes a replaceable propellant cartridge 12 which holds the propellant suspension under a suitable aerosolizing pressure. The suspension here is indicated at 14, and the liposomes in the suspension, at 16. The cartridge is equipped with a metering valve 18 which is designed to release a selected volume of the suspension, under pressure, when the valve is activated by being pushed inwardly. The cartridge is supported in a conventional atomizer 20 which functions to aerosolize the suspension released from the cartridge, on valve actuation, and direct the aerosol in a stream toward the user's mouth, which is may engage the mouthpiece 22 of the atomizer. Aerosol delivery devices of this type are well known.

The aerosol particles which are formed initially are propellant droplets containing the liposomes in suspended form. At these droplets are propelled through the air, the propellant rapidly evaporates, leaving an airborne suspension of liposome particles containing a selected dose of drug.

B. Liposome Entrainment in a Propellant

In this apparatus, or system, spray-dried liposomes containing a metered-dose quantity of drug are pre-packaged in dehydrated form in a delivery packet. The packet is used with a propellant spray device, to eject the liposome contents of the packet in an airborne suspension of liposome particles.

Figure 4:
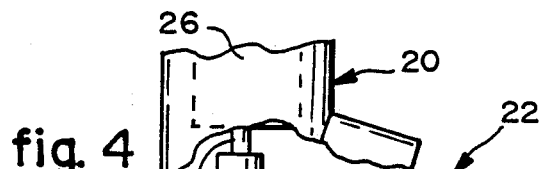
FIG. 4 is a side cutaway view of a liposome delivery apparatus constructed according to another embodiment of the invention, in which spray-dried liposomes are contained in a cylindrical packet, for entrainment in an aerosol stream produced by a self-contained propellant device.

FIG. 4 shows one embodiment of the system. The liposome packet shown here is a short length of tubing 22 containing a quantity of spray dried liposomes, indicated at 24, containing the metered dose of a selected drug. The packet, when supplied to the user, is sealed at its opposite ends to keep moisture out, and the liposomes are loosely held in the tubing, as shown. The seal is preferably a conventionally formed thin polymer barrier (not shown) which is easily rupturable at each tubing end to create an unobstructed passageway through the tubing.

The system also includes a propellant spray device 26 which contains a charge of pressurized propellant solvent, such as a Freon solvent, and which is equipped with a valve 28 for releasing a stream of aerosolized propellant. The downstream end of the valve terminates in a nozzle 30 which is adapted to receive an end of packet 22, as shown, to attach the packet operably to the device.

In operation, a packet is attached to the nozzle, preferably by inserting a sealed end of the packet tubing over the nozzle, to break the seal. The seal at the free end of the tubing is also punctured, for example, in the case of a friable seal, by pinching the tube end of the tubing. To deliver the liposome charge in the packet, the valve in the spray device is actuated briefly. It can be appreciated that the liposome in the packet become entrained in the stream of aerosolized solvent passing through the tubing. The solvent in turn rapidly evaporates, yielding an airborne suspension of the liposomes. Administration of the liposomes occurs, as above, by the user drawing in breath at the same time the liposome suspension is delivered. It will be understood that in its commercial embodiment, the device is supplied as a spray device with a plurality of liposome packets, one for each dosing.

Figure 5:
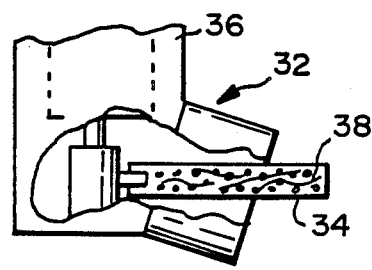
FIG. 5 is a side cutaway view of a liposome delivery apparatus like the one shown in FIG. 4, except where the liposomes are supported loosely on a porous matrix in a packet, for entrainment in an aerosol stream produced by a self-contained propellant device.

A second embodiment of the system is shown at 32 in FIG. 5. The system includes a liposome packet 34 which is adated for attachment to the nozzle of a valved spray device 36, as above. The system differs from the one described above in that the packet contains a loose matrix material or support 38 which allows an aerosol stream to pass through readily, but which acts to suspend and partially immobilize the dried liposome particles in the tube. The support shown in packet 34 is composed of a series of longitudinally extending, interconnected fibers 40. This system provide the potential for a more even distribution of aerosolized liposomes, and reduces the likelihood of liposome loss during setup.

C. Liposome Entrainment in Air

Figure 6:
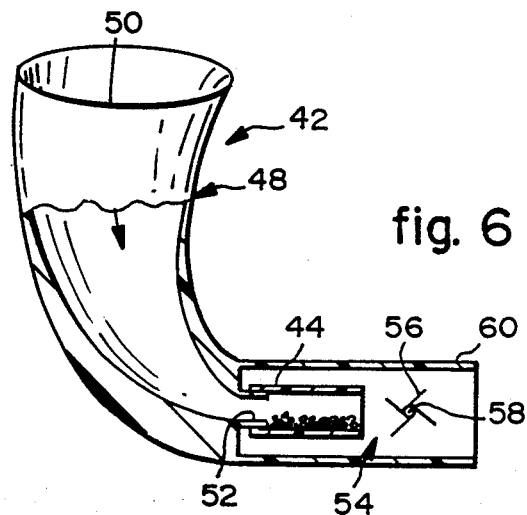
FIG. 6 is a side cutaway view of a liposome delivery apparatus constructed according to a third embodiment of the invention, in which spray-dried liposomes are contained in a capsule-like packet, and the packet is supported in the air passageway of a delivery device, for entrainment of the liposomes in a stream of air drawn through the passageway.

A third type of delivery apparatus or, system uses an airstream produced by user inhalation to entrain dried liposome particles and draw these into the user's respiratory tract. One exemplary system, based on a known type of aerosolizing device, is shown at 42 in FIG. 6. The liposome in this system are provided in moisture-free packets, such as packet 44, similar to packets 22 or 34 described above, each containing a metered dose of the drug in the liposomes.

A delivery device 46 in the system includes a curved pipe 48 which defines an inlet passageway 50 terminating at a reduced diameter nozzle 52 which is dimensioned to receive and hold packet 44, as shown. The other end of the pipe defines a convection region 54 where liposomes drawn out of the packet are distributed throughout the cross section of the downstream end of the pipe, while being drawn into the user's respiratory tract by inhalation. Air convection in the downstream pipe region is created by a paddle 56 which is freely rotatable on a shaft 58 supported within region 54. The pipe is provided with a mouthpiece 60 at its downstream end.

In operation, a packet is placed on the nozzle, preferably in a manner which rupture the seal at the "inner" end of the packet, as above, and the other end of packet is unsealed. The user now places his lips about the mouthpieces and inhales forcefully, to draw air rapidly into and through the pipe. As can be appreciated in the figure, the air drawn into the pipe becomes concentrated at the nozzle, creating a high-velocity airstream which carries liposomes out of the packet and into the convection region. The airstream and entrained liposomes impinge on the paddle, causing it to rotate and set up a convection within region 54. The liposomes are thus distributed more evenly, and over a broader cross section, just prior to being drawn into the user's respiratory tract by the inhalation.

As with the systems described in FIGS. 3-5, the system here is supplied to the user in the form of a single aerosol pipe with a plurality of single-dose packets.

III. Therapeutic Applications

A. Treatment of Bronchoconstriction

The present invention is useful in treating a variety of bronchoconstriction conditions, such as bronchial asthma, emphysema, bronchitis, and bronchiectasis. These conditions are responsive to $\beta_2$-agonists, which are also useful in treating peripheral vascular disease and shock, and may be used to delay delivery in cases of premature labor.

Earlier studies, reported in the above-cited co-pending patent applications for "Liposome Inhalation System and Method" have demonstrated three important advantages of liposome administration of $\beta_2$ agonist drugs to the respiratory tract. First, undesired side effects of the drugs, due to rapid systemic drug uptake, are largely eliminated or reduced, due to the much lower drug levels in the bloodstream which are observed after drug administration. In particular, "drug spiking" effects due to a large initial surge of systemic drug, and which are responsible for noticeable tachycardia, dizziness, and other $\beta_2$-agonist side effects, are largely avoided.

Another important advantage is that the drug, when administered in therapeutic dose via liposomes, shows more effective bronchodilation, at times greater than about 1 hour after drug administration, than a comparable amount of drug given in free form. This means that effective relief from asthma or other bronchoconstriction condition is provided with each administration, fewer drug administration are needed, and the patient is subject to less drastic swings in $\beta_2$ agonist levels in the body.

Thirdly, the rate of drug release from the site of administration in the lungs can be modulated, according to the lipid composition of the liposomes.

Delivery of drugs in a predominantly liposome-associate form solves a variety of problems encountered when the drug is administered in free of predominantly free form. In addition to the drug moderating and sustained-release features, the liposomes act to protect the drug from oxidation and protect the respiratory tract from potentially irritating drugs, particularly those which, because of solubility properties, must be administered in micronized form.

A variety of drugs effective in the treatment of bronchial or pulmonary conditions can be administered in the present system, with the same advantages. In one application for intrapulmonary drug delivery, α-1-protease inhibitor is delivered to the pulmonary interstitium in liposome-encapsulated form to stem the development of pulmonary emphysema. The liposomes act to protect the protease inhibitor's tertiary structure from oxidation, and facilitate its transport across the pulmonary cell membranes.

The present invention provides a convenient, self-contained system for administering liposome-encapsulated drugs to the respiratory tract drugs in a metered dose form. According to one advantage, the liposomes can be formulated to contain a desired ratio of encapsulated to non-encapsulated drug, depending on the drug ratio which is produced immediately before spray drying. This ratio determines the amount of drug which is delivered for rapid utilization in free drug form, versus that which is released slowly from the liposomes over a several hour period. In the specific example above, nearly half of the drug (MPS) was in non-encapsulated form at the time of spray drying. As seen above, this ratio was substantially preserved during the steps of suspension in a propellant solvent, aerosolization, and rehydration.

Another advantage of the system is that a relatively constant, and predictable drug dose can be administered with each dosing, since the amount of liposomes and entrapped drug remains substantially constant from one administration to another. The system is also convenient to use, since only a small, self-contained device—no larger than present propellant aerosol devices—is needed.

B. Sytemic-Action Drug Delivery

Many drugs whose primary mode of action requires uptake into the bloodstream can also be delivered by inhalation. The inhalation route allows the drug to be delivered rapidly to the bloodstream, is much more convenient to the patient than intramuscular or intravenous injection, and is suitable for drugs which cannot be delivered orally because of drug stability or the like. Heretofore, drug delivery by inhalation has been limited by a number of factors, including (a) lack of control of total drug dose, (b) inability to achieve long-term or controlled-release drug delivery, (c) the requirement for expensive and cumbersome inhalation equipment, for drugs which cannot be suspended in free form in a propellant solvent or are otherwise unstable in free form, (d) the extremely unpleasant taste of some drugs, and (e) drug irritation to the respiratory tract.

The present invention overcomes or minimizes many of the problems which have limited systemic drug delivery by inhalation heretofore. The problem of regulating drug dose is the most difficult of these, since variability in the amount of aerosolized material which actually reaches the respiratory tract, at a level which allows systemic uptake, will vary from one dosing to another. Nonetheless, some aspects of the liposome system are designed to facilitate more consistent total uptake. The liposomes themselves function as a bulking agent, i.e., solid particle carrier or filler, but because of the high concentration of drug which can be entrapped in the liposomes, much less particulate material may need to be administered. Accordingly, less total drug would be lost in "non-target" areas of the mouth and throat. In this regard it is noted that liposome surfaces can be made sticky to mucosal tissue, (as detailed in co-owned U.S. patent application for "Liposomes with Enhanced Retention on Mucosal Tissues", filed July 28, 1986, now U.S. Pat. No. 4,839,175 issued June 13, 1989 so that the liposomes themselves may be designed to effect drug release even if they did not reach the lower regions of the respiratory tract. Secondly, delivering a drug in particulate form from a propellant aerosol favors good drug uptake, and the present system allows many drugs, particularly lipid-soluble drugs and peptides, to be administered in this form.

As indicated above, the liposomal delivery system provides controlled-release systemic uptake, and the rate of uptake can be controlled, in the case of encapsulated water-soluble drugs, by the lipid composition of the liposomes. Earlier experiments conducted by the inventors have shown that aerosol delivery of drugs can reduce initial rate of systemic uptake at least about 8 fold, and also produce more even drug plasma levels over an extended period following drug delivery.

The system of the invention allows both water-soluble and lipid soluble drugs to be delivered from a convenient, relatively inexpensive self-contained delivery device. As indicated above, the drug in liposome entrapped form may be more stable, less irritating to the respiratory tract when administered. Further the taste of the drug may be substantially masked in liposome entrapped form.

An example of a specific application for systemic drug delivery is the encapsulation and delivery of nitroglycerin, a coronary vasodilator used to relieve the symptoms of angina pectoris. The drug formulation typically will contain about 30%–40% free drug, which can be rapidly absorbed by the pulmonary blood flow and transported directly to the heart, its primary site of action, to provide immediate relief from the chest pain associated with angina. The remaining 60%–70% or more of the liposome-encapsulated drug can be is released slowly, at a rate controlled by liposome composition, to afford prolonged coronary vasodilation, and thus relief from chest pain for an extended period.

Oxytocin, a peptide hormone that induces and augments the strength of uterine muscle contractions during labor, can be formulated and delivered in a manner similar to that described for nitroglycerin. It is currently delivered by intravenous infusion, a process that requires placement and maintenance of a venous cannula, a sometimes difficult procedure that limits the patient movement and posture. Aerosols of liposome-oxytocin formulation would provide immediate and sustained delivery to the systemic circulation, similar to that provided by IV infusion, without restricting patient motion. A wide range of other systemic-acting drugs, such as those named above in Section I, could also be administered advantageously by the system of the invention.

While preferred embodiments, uses, and methods of practicing the present invention have been described in detail, it will be appreciated that various other uses, formulations, and methods of practice as indicated herein are within the contemplation of the present invention.

It is claimed:

1. Apparatus for administering a water-soluble drug, at a selected dose, via the respiratory tract comprising
dehydrated liposome particles formed by the steps of
(a) producing a liposome suspension having at least about 50% liposome-encapsulated drug, and (b) dehydrating the suspension, and a device for producing an airborne suspension of the liposome particles containing such selected dose of the drug.

2. The apparatus of claim 1, wherein the liposomes are composed predominantly of saturated or partially saturated phospholipids.

3. The apparatus of claim 1, wherein the liposomes are suspended in a fluorocarbon propellant solvent, and said device includes a cannister containing the liposome/propellant suspension in pressurized form, and a valve connected to the cannister for delivering a selected volume of the suspension in aerosolized form.

4. The apparatus of claim 3, wherein the propellant is selected from the group consisting of $CCl_2F_2$, $CClF_2CClF_2$, and $CClF_2CF_3$.

5. The apparatus of claim 3, wherein the liposome particles are formed by dehydrating the liposomes by spray drying, and the liposomes are composed predominantly of phospholipids whose phase transition provides protection to drying at temperatures above about 40° C.

6. The system of claim 3, for use in delivering a lipid soluble drug selected from the group consisting of prostaglandins, amphotericin B, progesterone, isosorbide dinitrate, testosterone, nitroglycerin, estradiol, doxorubicin, beclomethasone and esters, vitamin E, cortisone, dexamethasone and esters, DPPC/DPPG phospholipids, and betamethasone valerete, wherein the drug is present predominantly in propellant-solubilized form, and becomes entrapped in liposomes upon aerosolization and evaporation of the propellant.

7. The apparatus of claim 1, wherein the liposomes are contained in dehydrated packets, each packet containing such selected amount of the drug in liposome-entrapped form, and said device includes means for expelling the liposomes from the packet in an air-borne form.

8. The apparatus of claim 7, wherein said device is a spray device containing a pressurized fluorocarbon propellant, a valve for releasing the pressurized propellant in an aerosolized stream, and means connecting the valve to a liposome packet, effective to bring the aerosolized propellant stream into contact with the liposomes in the packet, to entrain the liposomes in the propellant stream.

9. The apparatus of claim 8, wherein each packet includes a porous matrix on which the liposomes are supported and through which the stream is directed.

10. The apparatus of claim 7, wherein said device defines air passageway adapted to hold a packet, to allow a stream of air drawn into the passageway to entrain the liposomes.

11. The apparatus of claim 7, wherein the drug is selected from the group consisting of terbutaline, albuterol (salbutamol) sulfate, ephidrine sulfate, ephidrine bitartrate, isoetharine hydrochloride, isoetharine mesylate, isoproteranol hydrochloride, isoproteranol sulfate, metaproteranol sulfate, terbutaline sulfate, procaterol, bitolterol mesylate, atropine methyl nitrate, cromolyn sodium, propranalol, fluroisolide, ibuprofin, gentamycin, tobermycin, pentamidine, penicillin, theophylline, bleomycin, etoposide, captopril, n-acetyl cysteine, verapamil, calcitonin, atriopeptin, α-1 antitrypsin (protease inhibitor), interferon, vasopressin, insulin, interleukin-2, superoxide dismutase, tissue plasminogen activator (TPA), plasma factor 8, epidermal growth factor, tumor necrosis factor, heparin, lung surfactant protein, and lipocortin.

12. A method for administering a water-soluble drug, at a selected dose, to the respiratory tract comprising
providing dehydrated liposome particles formed by the steps of (a) producing a liposome suspension having at least about 50% liposome-encapsulated drug, and (b) dehydrating the suspension, and
producing an airborne suspension of the liposome particles containing the selected dose of the drug.

13. The method of claim 12, wherein the liposome particles are formed by dehydrating the liposomes by spray drying, and the liposomes are composed predominantly of phospholipids which provide protection against liposome disruption on drying in a stream of gas at a temperature above about 37° C.

14. The method of claim 12, wherein the liposomes are suspended in a fluorocarbon propellant, and, and said producing includes storing the suspension under pressure in a cannister, and releasing a selected amount of the suspension from the cannister in an aerosolized form.

15. The method of claim 14 for use in administering a water-soluble drug selected from the group consisting of terbutaline, albuterol (salbutamol) sulfate, ephidrine sulfate, ephidrine bitartrate, isoetharine hydrochloride, isoetharine mesylate, isoproteranol hydrochloride, isoproteranol sulfate, metaproteranol sulfate, terbutaline sulfate, procaterol, bitolterol mesylate, atropine methyl nitrate, cromolyn sodium, propranalol, fluroisolide, ibuprofin, gentamycin, tobermycin, pentamidine, penicillin, theophylline, bleomycin, etoposide, captopril, n-acetyl cysteine, and verapamil, wherein the drug is present in the suspension predominantly in liposome entrapped form.

16. The method of claim 12, wherein the liposomes are contained in dehydrated packets, each packet containing the selected amount of the drug in liposome-entrapped form, and said producing includes expelling the liposomes from the packet in an air-borne form.

17. The method of claim 16, wherein said producing includes spraying a stream of aerosolized fluorocarbon solvent through the packet, to entrain liposomes in the packet in the stream.

18. The system of claim 12, wherein the drug is selected from the group consisting of terbutaline, albuterol (salbutamol) sulfate, ephidrine sulfate, ephidrine bitartrate, isoetharine hydrochloride, isoetharine mesylate, isoproteranol hydrochloride, isoproteranol sulfate, metaproteranol sulfate, terbutaline sulfate, procaterol, bitolterol mesylate, atropine methyl nitrate, cromolyn sodium, propranalol, fluroisolide, ibuprofin, gentamycin, tobermycin, pentamidine, penicillin, theophylline, bleomycin, etoposide, captopril, n-acetyl cysteine, verapamil, calcitonin, atriopeptin, α-1 antitrypsin (protease inhibitor), interferon, vasopressin, insulin, interleukin-2, superoxide dismutase, tissue plasminogen activator (TPA), plasma factor 8, epidermal growth factor, tumor necrosis factor, heparin, lung surfactant protein, and lipocortin.

* * * * *

UNITED STATES PATENT AND TRADEMARK OFFICE
CERTIFICATE OF CORRECTION

PATENT NO. : 4,895,719

DATED : January 23, 1990

INVENTOR(S) : Ramachandran Radhakrishnan; Paul J. Mihalko, Robert M. Abra

It is certified that error appears in the above-identified patent and that said Letters Patent is hereby corrected as shown below:

Column 1, line 25, change the numeral "344" to --355--; and

Column 5, line 20, change the "+" to --°--; and

Signed and Sealed this

Seventeenth Day of December, 1991

Attest:

HARRY F. MANBECK, JR.

Attesting Officer

Commissioner of Patents and Trademarks